United States Patent [19]

Hisatomi et al.

[11] Patent Number: 5,055,245
[45] Date of Patent: Oct. 8, 1991

[54] METHOD OF MEASURING TEMPERATURE WITHIN CURED ARTICLE AND METHOD OF CONTROLLING TIRE VULCANIZATION

[75] Inventors: Hideo Hisatomi, Kodaira; Toshiro Iwata, Musashimurayama; Toshihide Kosoegawa, Shiki; Kikuo Oka, Higashimurayama; Seizo Ichikawa; Kuninori Mitarai, both of Kodaira, all of Japan

[73] Assignee: Bridgestone Corporation, Tokyo, Japan

[21] Appl. No.: 330,948

[22] Filed: Mar. 23, 1989

Related U.S. Application Data

[63] Continuation of Ser. No. 69,799, Jul. 6, 1987, abandoned.

[30] Foreign Application Priority Data

| Jul. 7, 1986 | [JP] | Japan | 61-160580 |
| Jul. 8, 1986 | [JP] | Japan | 61-161559 |
| Oct. 28, 1986 | [JP] | Japan | 61-257740 |
| Dec. 2, 1986 | [JP] | Japan | 61-288525 |

[51] Int. Cl.[5] .................................. B29C 35/04
[52] U.S. Cl. .............................. 264/40.6; 264/315; 264/326; 425/29; 425/42; 425/143; 425/162
[58] Field of Search ............ 264/40.1, 40.6, 315, 264/326; 425/29, 143, 170, 42, 30, 162

[56] References Cited

U.S. PATENT DOCUMENTS

| 3,649,729 | 3/1972 | Davis et al. | 264/315 |
| 4,371,483 | 2/1983 | Mattson | 264/40.6 |
| 4,422,987 | 12/1983 | Arimatsu | 264/40.6 |

Primary Examiner—Jan H. Silbaugh
Assistant Examiner—Mathieu Vargot
Attorney, Agent, or Firm—Sughrue, Mion, Zinn Macpeak & Seas

[57] ABSTRACT

In a method of controlling a tire vulcanization by controlling a heat supply to a vulcanizing machine including a mold unit and a bladder unit, temperatures at points on a boundary between the mold unit and a tire are measured by means of temperature sensors, a temperature at a center post assembly of the bladder unit is measured by a temperature sensor arranged at the center post assembly. The method includes calculating temperature profiles within the tire from the measured temperatures by using the finite difference method, estimating vulcanization profiles within the tire from the temperature profile, deriving the least vulcanization within the tire from the vulcanization profiles, and producing a stop signal for the heat supply to the vulcanizing machine in accordance with the least vulcanization thus derived.

18 Claims, 13 Drawing Sheets

METHOD OF MEASURING TEMPERATURE WITHIN CURED ARTICLE AND METHOD OF CONTROLLING TIRE VULCANIZATION

This is a continuation of Ser. No. 069,799, filed on July 6, 1987, now abandoned.

BACKGROUND OF THE INVENTION

Field of the Invention and Related Art Statement

The present invention generally relates to a technique for curing or vulcanizing rubber or plastic articles and more particularly to a method of measuring a temperature at a point within a rubber or plastic article during a vulcanization. This invention also relates to a method of controlling the vulcanization of a pneumatic tire.

In the pneumatic tire manufacturing process, a green tire is placed in a vulcanizing machine and is subjected to heat and pressure. In order to manufacture a tire having desired characteristics, it is important to control the vulcanizing process in an accurate and reliable manner. In the known curing process the temperature of a vulcanizing mold and temperature and pressure inside a bladder are kept constant and heating and pressing are carried out for a predetermined time period. In practice, temperatures at various points within the tire vary due to variations of various factors such as variations in construction of green tires, mold temperature and bladder temperature and pressure. These variations may fluctuate day by day as well as season by season. Therefore, in the known method, in order to avoid undesired variations under vulcanization, the curing time period has to be set longer than may be necessary. Then, undesired over cure might occur and the desired characteristics of tire could not be attained. Moreover, the longer curing time reduces the manufacturing efficiency and requires a greater amount of heating fluid.

In order to mitigate the above mentioned drawback, there have been proposed various methods of controlling the vulcanizing process. For instance, in U.S. Pat. No. 3,819,915, there is disclosed a method of controlling the vulcanization, in which a temperature at a point within a tire set in the vulcanizing machine is detected by selectively inserting a thermometer into the tire and the vulcanized condition of the tire is judged on the basis of the detected temperature. However, in such a method since the thermometer is inserted into the tire, a trace of the thermometer insertion remains in a surface of the vulcanized tire and the commercial value of tire might be decreased. Further, it is rather difficult to measure a true temperature of the tire in a precise manner by inserting the thermometer into the tire. Moreover, since only a temperature at the predetermined point within the tire can be measured, a temperature at a point where the vulcanization has been effected to the least extent (point of least vulcanization) could not be detected, so that the vulcanization could not be controlled precisely. It is apparent that the operation of inserting and pulling the thermometer into and from the tire is very cumbersome and the thermometer might be broken easily. Further in this known method since the thermometer is inserted into the outer surface of the tire, it is impossible to detect temperatures at various points within the tire.

In U.S. Pat. No. 3,649,729 there is described another known method of controlling the vulcanization. In this method, a temperature at a boundary between the tire and mold and a temperature at boundary between the tire and bladder are measured and temperatures at points within the tire are calculated from the above detected temperatures at the boundaries, and then vulcanization of tire is estimated from the calculated temperatures.

In this known method, it is essential to use temperature sensors locatable at the boundaries between the tire and the mold and bladder, respectively. However, in practice, it is almost impossible to locate the temperature sensor at the boundary between the tire inner surface and an outer surface of the bladder. If use is made of an expansible bladder made of rubber, the temperature sensor could never be applied onto the outer surface of the bladder. Although the temperature sensor may be secured on a foldable bladder, the bladder has to be exchanged by new one after using it only for a few days, so that the temperature sensor would be also wasted. Therefore, such a method could not be performed economically. Further the maintenance of the temperature sensor would be very cumbersome.

In the above mentioned known methods, the degree of tire vulcanization is estimated on the basis of the well-known Arrhenius equation, while the point of least vulcanization is assumed to be remained at a fixed point. However, in practice, the point of least vulcanization varies during the curing process, so that the vulcanization could not be detected in an accurate manner.

In U.S. Pat. No. 4,371,483, there is disclosed still another method of controlling the vulcanization. In this method, a temperature profile within the tire is calculated by measured temperatures and a point of least vulcanization is derived from the temperature profile. Therefore, the point of least cure can be traced during the vulcanization. However, in this method, temperatures at the boundaries between the tire and the mold and bladder could not be measured accurately. That is to say, the temperature at the boundary between the mold and the outer surface of the tire is estimated by measuring a temperature on an outer surface of the mold. However, the temperature on the outer surface of the mold does not reflect the temperature at the outer surface of tire, because the temperature on the outer surface of mold would be varied in accordance with an ambient temperature. Further, in this known method, the temperature at the boundary between the inner surface of the tire and the bladder is estimated from or temperature at a supply or drain pipe for introducing or discharging the heated fluid into or out of the inside of the bladder. However, the temperature at the pipe outside the bladder could never represent the temperature at the boundary between the tire and the bladder. Particularly, in case of using steam and/or gas as the heating fluid medium passing through the bladder, the temperature at the boundary between the inner surface of tire and the bladder could never be estimated from the temperature at the pipe connected to the bladder.

Therefore, in the known method, the temperatures at points within the tire could not be estimated in an accurate manner, so that vulcanization could not be controlled precisely.

Further, in the method disclosed in the above mentioned U.S. Pat. No. 4,371,483, the state of cure at a tire shoulder is calculated by a finite element method using a finite number of rules and steps. However, in the finite element method, a plurality of coefficients have to be calculated by using a large scale computer for respective kinds of tires to be cured, so that the process becomes quite complicated and cumbersome. Moreover, the point of least vulcanization is not always existent at the shoulder, so that this method could be applied only to limited kinds of tires.

SUMMARY OF THE INVENTION

The primary object of the invention is to provide a method of detecting in an accurate and reliable manner a temperature at a point within a rubber or plastic article which is cured by a vulcanizing machine having a mold unit for heating the article and defining an outer configuration of the article and a bladder unit for heating the article and pressing the article against the mold unit.

It is another object of the invention to provide a novel and useful method of controlling the tire vulcanization, in which any undesired under or over cure can be prevented effectively in spite of variations in various factors such as green tire temperature, kinds of tires, mold temperature and bladder temperature and pressure.

According to the invention, a method of detecting a temperature at at least one point within a rubber or plastic article cured by a vulcanizing machine having a mold unit for heating the article and defining an outer configuration of the article and a bladder unit for heating the article and pressing the article against the mold unit, comprises the steps of:

effecting a temperature measurement with the aid of a temperature sensor arranged at or near a boundary between the mold unit and the article to provide a first temperature;

effecting a temperature measurement with the aid of a temperature sensor arranged on a central post assembly of the bladder unit to provide a second temperature; and calculating temperature at a point within the article on the basis of said first and second temperatures.

According to the invention, a method of controlling a tire vulcanization by controlling a heat supply to a vulcanizing machine which includes a mold unit and a bladder unit having a bladder and a center post assembly comprises the steps of:

measuring a first temperature at at least one point at or near a boundary between the mold unit and the tire during the tire vulcanization with the aid of a first temperature sensing means;

measuring a second temperature at the center post assembly of the bladder unit during the tire vulcanization with the aid of a second temperature sensing means;

calculating a temperature profile within the tire from said first and second temperatures;

estimating a vulcanization profile within the tire from said temperature profile;

detecting a least vulcanization of said vulcanization profile within the tire; and determining a timing at which the heat supply to the vulcanizing machine is stopped in accordance with said least vulcanization within the tire.

DESCRIPTION OF THE PREFERRED EMBODIMENTS

Figure 1:
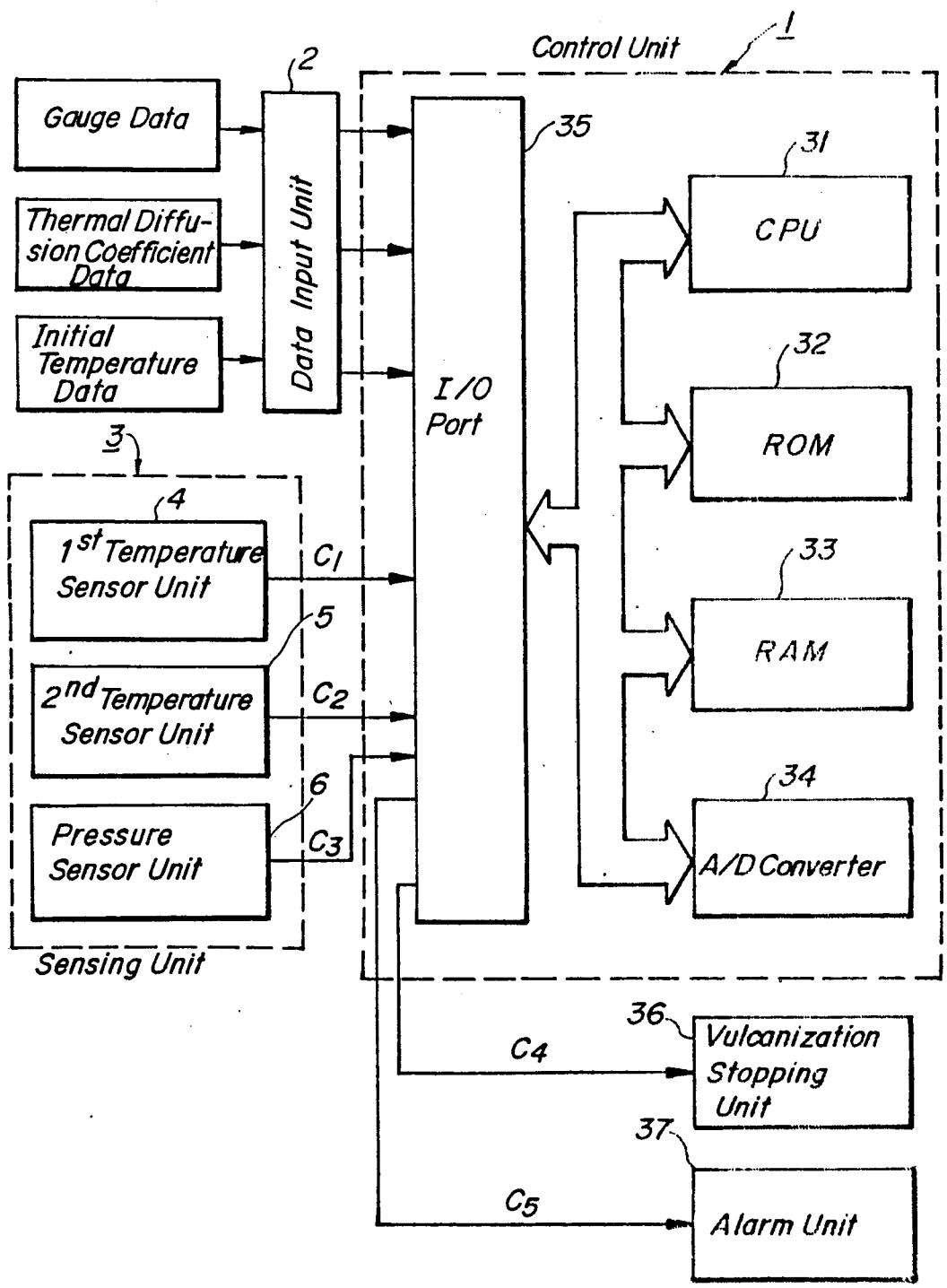
FIG. 1 is a block diagram showing the apparatus for carrying out the tire vulcanization controlling method according to the invention.

FIG. 1 is a block diagram showing an embodiment of the apparatus for carrying out the tire vulcanization controlling method according to the invention. The apparatus comprises control unit 1, input unit 2 such as keyboard, input card and simple setting display panel for entering various kinds of data from the external, and sensing unit 3 comprising a first temperature sensor unit 4 for measuring temperatures at a boundary between a tire and a mold unit, a second temperature sensor unit 5 for measuring a temperature at a center post assembly of a bladder unit and a pressure sensor unit 6 for measuring a pressure inside a bladder.

Figure 2:
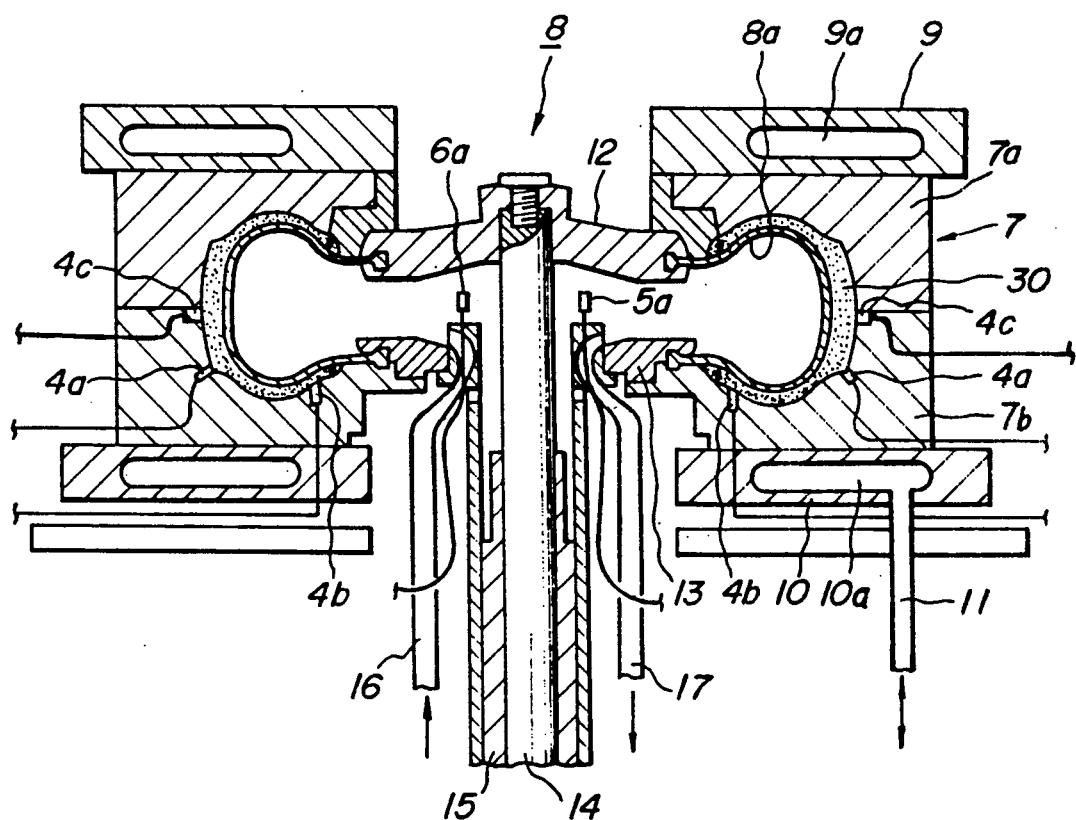
FIG. 2 is a schematic cross sectional view illustrating the construction of the vulcanizing machine.

FIG. 2 is a schematic cross sectional view showing a vulcanizing machine. The vulcanizing machine comprises a vulcanizing mold unit 7 and a bladder unit 8 having a deformable bladder 8a. The mold unit 7 comprises upper and lower mold halves 7a and 7b. In order to heat the mold unit 7, upper and lower platens 9 and 10 are arranged above and below the mold unit, respectively. The platens 9 and 10 have passages 9a and 10a formed therein, and through the passages is circulated a heated fluid via a pipe 11 as shown by a double-headed arrow in FIG. 2. The bladder 8a is secured to upper and lower rings 12 and 13, and the upper ring 12 is secured to a center post 14 which is movably supported by a sleeve 15. Therefore, the bladder 8a can be moved in accordance with up and down movement of the center post 14. The lower ring 13 are connected to pipes 16 and 17 for circulating a heated fluid medium such as steam, gas and water through the inner space of the bladder 8a. The first temperature sensor unit 4 comprises a plurality of temperature sensors 4a arranged equidistantly along a shoulder of tire, a plurality of temperature sensors 4b arranged equidistantly along a bead of tire, and a plurality of temperature sensors 4C arranged equidistantly along a tread of tire.

The second temperature sensor unit 5 comprises a single temperature sensor 5a for measuring the temperature of the heated fluid medium within the bladder 8a. According to the invention, this temperature sensor 5a is arranged at a center post assembly of the bladder unit 8, i.e. to the lower ring 13. The pressure sensor unit 6 has a pressure sensor 6a which is also secured to the center post assembly.

Figure 3:
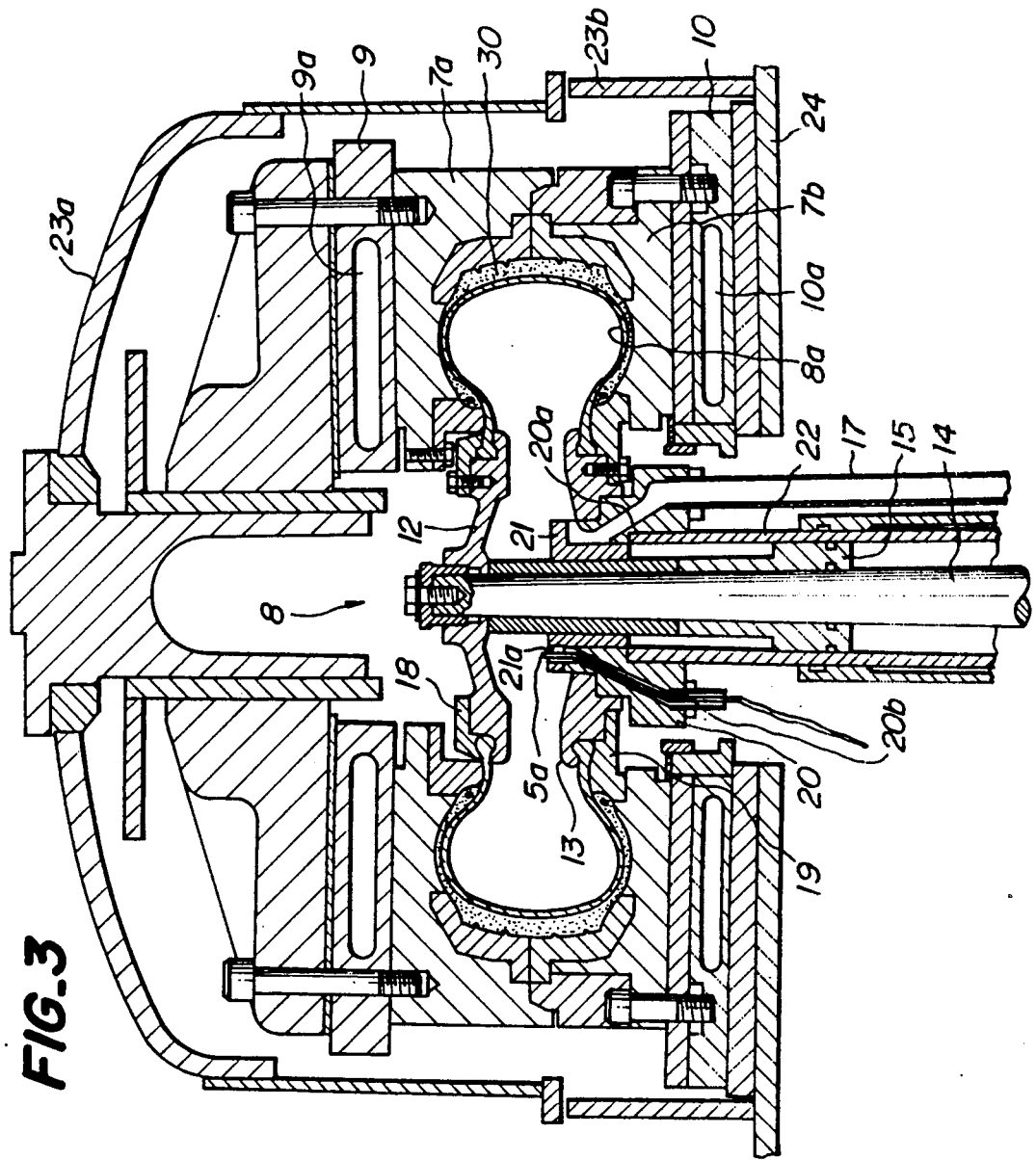
FIG. 3 is a cross sectional view depicting the construction of the vulcanizing machine in greater detail.

FIG. 3 is a cross sectional view showing detail of the construction of the vulcanizing machine. Particularly, in FIGS. 3, a manner of securing the temperature sensor 5a to the center post assembly is shown clearly. The upper ring 12 is secured to the top end of the center post 14 so that the upper ring is moved up and down together with the center post. An upper ridge of the bladder 8a is clamped between the upper ring 12 and an upper clamping ring 18. A lower ridge of the bladder 8a is clamped between the lower ring 13 and a lower clamping ring 19. The lower ring 13 is screwed to a manifold block 20 to which is secured a sleeve 21 and a bag cylinder 22. The pipe 17 is communicated with the inner space of the bladder 8a via a conduit 20a formed in the manifold block 20. The temperature sensor 5a is passed through a hole 21a formed in the sleeve 21 and a conduit 20b formed in the manifold block 20. The pressure sensor 6a is provided in a similar manner to that explained above.

The upper mold half 7a and upper platen 9 are connected to an upper dome 23a, and a lower dome 23b is secured to a base 24 to which are also connected the lower mold half 7b and lower platen 10.

Figure 4:
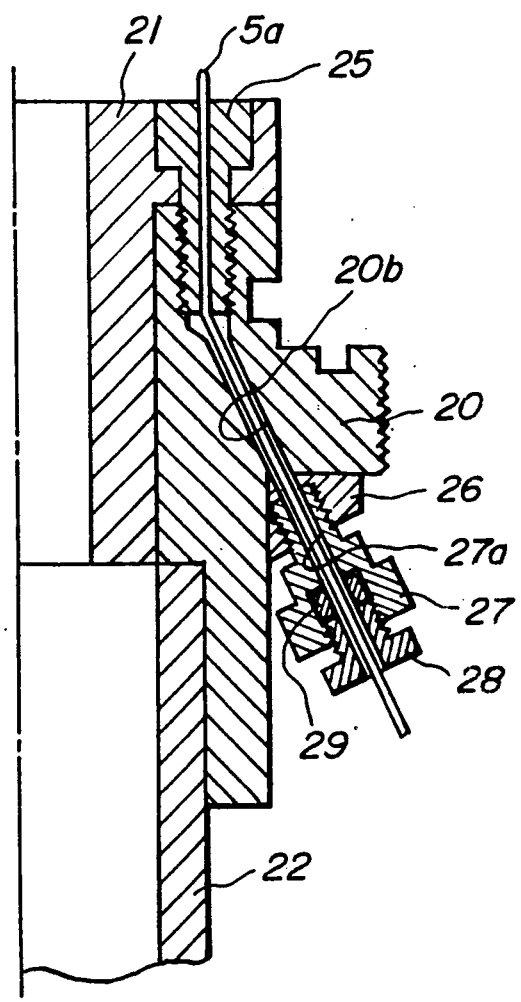
FIG. 4 is a cross sectional view illustrating a part of the center post assembly of the bladder unit.

FIG. 4 is a cross sectional view showing a more detailed construction of the center post assembly for securing the temperature sensor 5a. To the bag cylinder 22 is soldered the manifold block 20 to which is also soldered the sleeve 21. In the sleeve 21 there is formed the hole 21a in which is inserted a bolt 25 having a hole formed therein, and the bolt is screwed to the manifold block 20. To a lower corner of the manifold block 20 is soldered a ring 26 to which is screwed a bolt 27 having a central hole 27a which is communicated with the hole 20b formed in the manifold block 20. Into a top hole of the bolt 27 is further screwed a bolt 28 via a sealing ring 29. In this manner, the temperature sensor 5a can be firmly secured to the center post assembly of the bladder unit in an air tight manner without modifying the existing bladder unit to a large extent. Further, the temperature sensor 5a can be easily exchanged without decomposing the bladder unit so that the maintenance of the sensor 5a is very easy.

After a green tire to be cured has been placed in the vulcanizing machine and the upper and lower mold halves 7a and 7b have been closed, the heated fluid is passed through the passages 9a and 10a of platens 9 and 10 to heat the tire 30 from the outside thereof. At the same time, the heated fluid medium is circulated through the inside space of the bladder 8a via the pipes 16 and 17 to expand the bladder toward the mold unit 7 and to heat the tire 30 from the inside thereof. When the bladder 8a is expanded, the tire 30 is pressed against the inner wall of the mold unit 7 to define an outer configuration of the tire.

According to the present embodiment during the vulcanizing operation, the temperature at the boundary between the mold unit 7 and the tire 30 and at the center post assembly of the bladder unit 8 are measured by means of the first and second temperature sensing units 4 and 5. At the same time, the pressure sensor unit 6 measures the pressure inside the bladder 8a. Signals $C_1$, $C_2$ and $C_3$ representing the temperatures and pressure measured by these sensor units 4, 5 and 6 are supplied to the control unit 1.

As illustrated in FIG. 1, the control unit 1 comprises CPU 31, ROM 32, RAM 33, A/D converter 34 and I/O port 35. CPU 31 takes necessary data from I/O port 35 in accordance with a program stored in ROM 32 and effects various operations and calculations to derive various signals for controlling the tire vulcanization, while data is transferred between CPU 31 and RAM 33. The signals thus calculated are supplied to I/O port 35. A/D converter 34 converts signals supplied to I/O port 35 into digital signals under the command from CPU 31. ROM 32 stores the necessary operation programs for CPU 31, and RAM 33 stores calculating programs and data in the form of map.

Various kinds of initial data are entered into the control unit 1 by means of the data input unit 2. That is to say, gauge data expressing thicknesses of tire 30 and bladder 8a, thermal diffusion coefficient data, and initial temperature data are entered into the control unit 1 via the input unit 2.

The control unit 1 calculates a temperature profile within the tire 30 and derives a point of least cure in the manner explained below at the commencement of each predetermined time interval. When a predetermined vulcanization is attained, the control unit 1 supplies a control signal $C_4$ to a vulcanization stopping unit 36. When the control unit 1 detects any abnormal condition, it supplies a signal $C_5$ to an alarm unit 37 to generate or display alarm.

Now the process of deriving the temperature profile within the tire and of deriving the least cure point will be explained.

Figure 5:
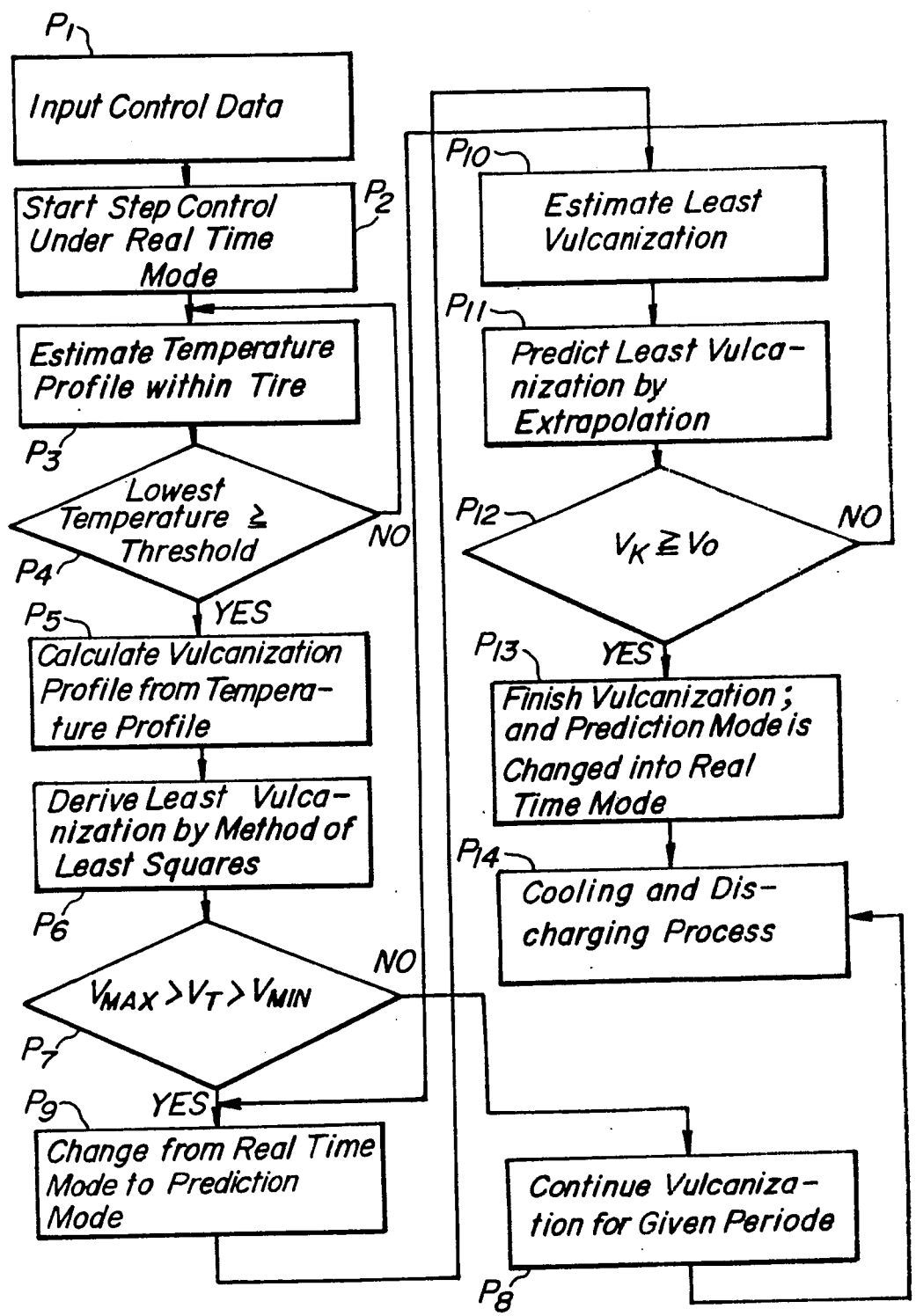
FIG. 5 is a flow chart representing successive steps of an embodiment of the tire vulcanization controlling method according to the invention.

FIG. 5 is a flow chart showing successive steps of the process. Prior to the actual vulcanization, the data necessary for the calculation and control is entered into the control unit 1 with the aid of the input unit 2 as shown by a step $P_1$. That is to say, thicknesses and thermal diffusion coefficients of the tire 30, bladder 8a and boundary layers, and initial temperatures of tire are entered as the initial data as will be explained more in detail later. Further, data identifying a real time control mode and a prediction control mode is read into the control unit 1. From the start of the vulcanization, the temperatures and pressures are measured, and at the same time the elapsed time is measured.

At a step $P_2$, the tire is heated and cured under the real time control mode. That is to say, the heated fluid medium is supplied to the passages 9a, 10a of the platens 9, 10, and the heated fluid medium such as steam and gas is circulated under a pressure through the inside of the bladder 8a to heat the tire 30 from both the outside and inside thereof, while the tire 30 is pressed against the inner surface of the mold unit 7.

During vulcanization, the temperatures at the boundary between the mold unit 7 and the tire 30 and the temperature at the center post assembly of the bladder unit 8 are entered into the control unit 1 at a unit time interval $\Delta\theta$. This unit time interval $\Delta\theta$ may be selected at will in accordance with a desired precision of the control. In the present embodiment, the temperatures at the shoulder, bead and tread of the tire 30 are measured by means of the temperature sensors 4a, 4b and 4c.

In a step $P_3$, temperatures at points within the tire 30 are calculated and estimated to derive temperature profiles within the tire 30 at the shoulder, bead and tread at the commencement of each time internal $\Delta\theta$. Hereinafter the process of deriving the temperature profile at the shoulder will be explained.

In the present embodiment, the temperature at the boundary between the mold unit 7 and the tire 30 is measured by providing the temperature sensors 4a, 4b, 4c at this boundary. The inventors have conducted various experiments and have found that it is very difficult to measure a true temperature at the boundary in a precise manner.

Figure 6:
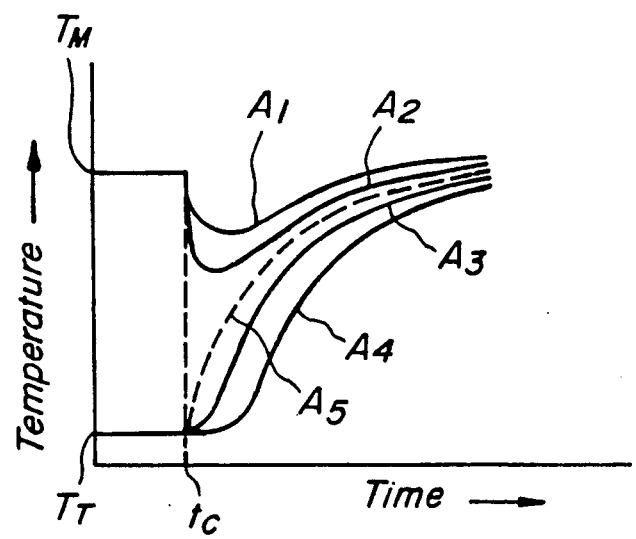
FIG. 6 is a graph showing temperature variations measured by temperature sensors arranged at various positions.

FIG. 6 is a graph expressing temperature variations when the temperature sensor is provided at various points. When the temperature sensor is secured to the mold in such a manner that its temperature sensitive chip is retarded from the inner surface of the mold by 0.5 mm, the temperature changes as shown by a curve $A_1$. In FIG. 6, a temperature $T_M$ is an initial mold temperature, $T_T$ is an initial tire temperature and $t_C$ represents a timing when the mold is brought into contact with the tire. When the temperature sensor is fixed to the mold such that its temperature sensitive chip is just aligned with the inner surface of the mold, the temperature varies as illustrated by a curve $A_2$. When the temperature sensor is secured to the tire, while its temperature sensitive chip is aligned in the surface of tire, the temperature change is expressed by a curve $A_3$. A curve $A_4$ represents a temperature variation when the temperature sensor is secured to the tire such that the temperature sensitive chip is kept back from the surface of tire by 0.5 mm. In FIG. 6 there is also shown a true temperature variation at the boundary by a broken curve $A_5$. When the temperature sensor is secured to the mold, the measured temperature is higher than the true temperature, and when the temperature sensor is installed in the tire, the detected temperature is lower than the true temperature. At any rate, it is practically impossible to measure the true temperature at the boundary between the mold and the tire. Therefore, in the present embodiment, there is introduced a boundary layer between the mold and the tire. Owing to the same reason, there is also introduced a boundary layer between the temperature sensor 5a and the bladder 8a.

Figure 7:
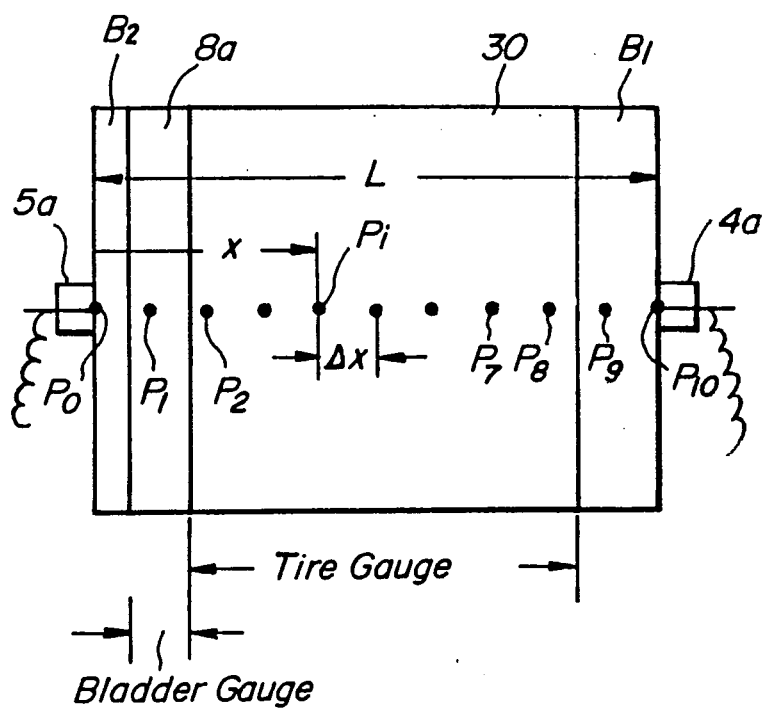
FIG. 7 is a schematic view showing a thermal diffusion model adopted by the method according to the invention.

FIG. 7 is a schematic view showing a heat transfer model constructed by taking into account of the two boundary layers according to the invention. That is to say, the first boundary layer $B_1$ is interposed between the temperature sensor 4a and the tire 30 and the second boundary layer $B_2$ is placed between the bladder 8a and the temperature sensor 5a. A thickness of the first boundary layer $B_1$ is determined by a material of the mold unit 7, kind and sensitivity of the temperature sensor 4a, and a distance from the inner surface of the mold to the heat sensitive chip of the temperature sensor 4a. A thickness of the second boundary layer $B_2$ is determined by the kind, sensitivity and position of the temperature sensor 5a, and the condition of heated fluid, i.e. material of the fluid, agitation and the like. It should be noted that the thicknesses of the boundary layers $B_1$ and $B_2$ may be previously determined experimentally.

Next, in a step $P_3$, the temperature profile or distribution within the tire 30 is calculated on the basis of the thermal diffusion theory by taking into account of the following elements a)~e).

Element a) Gauge Data

The gauges, i.e. the thicknesses of the tire 30 and bladder 8a are actually measured or calculated. The gauges of the first and second boundary layers $B_1$ and $B_2$ can be determined by considering various factors such as the mold material, kinds, sensitivity and position of the temperature sensors 4a, 5a, kind of heated fluid such as steam, gas and water and supply conditions of heated fluid such as supply time period and mixing ratio. In practice, the gauges of the boundary layers $B_1$ and $B_2$ are determined experimentally. These gauge values are entered into the control unit 1 with the aid of the input unit 2.

Element b) Thermal Diffusion Coefficient Data

As will be explained later the temperature within the tire 30 is estimated by the finite difference method. However, since the tire has a complex construction composed of a plurality of different constructional elements, it is impossible to derive the temperature profile by the finite difference method. Therefore, in the present embodiment, there is introduced an average thermal diffusion coefficient. In order to derive the average thermal diffusion coefficient, thermal diffusion coefficients of various components constructing the tire are entered into the control unit 1 via the input unit 2. It is now assumed that $\alpha_1 \sim \alpha_5$ and $G_1 \sim G_5$ are thermal diffusion coefficients and thicknesses of the first boundary layer $B_1$, tread and carcass of the tire 30, bladder 8a and second boundary layer $B_2$. Then the average thermal diffusion coefficient $\alpha$ can be calculated by the following equation:

$$\overline{\alpha} = \frac{\sum_{i=1}^{5} \alpha_i \cdot G_i}{\sum_{i=1}^{5} G_i}$$

The thermal diffusion coefficient $\alpha_i$ may be derived from the following equation.

$$\alpha_i = \frac{K_i}{C_{pi} \cdot \rho_i}$$

wherein
$K_i$ ... thermal conductivity
$C_{pi}$ ... specific heat
$\pi_i$ ... density Element c) Initial Temperature Data Prior to vulcanization, surface temperatures of the bladder 8a and the green tire are measured by a non-contact type infra-red thermometer or a contact type thermometer and the measured temperatures are entered into the control unit 1 by means of the input unit 2.

Element d) Measured Data

The temperatures at the boundary between the mold unit 7 and the tire 30 and at the center post assembly of the bladder unit 8 are measured by the sensors 4a and 5a, and the signals $C_1$ and $C_2$ representing measured temperatures are supplied to the control unit 1.

In the present embodiment, the signal $C_3$ representing the bladder pressure measured by the pressure sensor 6a is also supplied to the control unit 1.

Element e) Estimation of Temperature within Tire

On the basis of the above mentioned data entered into the control unit 1, the temperature profile within the tire 30 is estimated by the control unit. The estimating calculation may be effected by the finite element method (FEM) or the finite difference method (FDM).

Now the finite difference method will be explained. In order to shorten the calculating time, the one-dimensional model shown in FIG. 7 is considered and temperatures at a given finite number of points $P_1$, $P_2$ . . . within the tire 30 is calculated. These points are separated from each other by a given constant distance $\Delta x$ as shown in FIG. 7. In the present embodiment, the entire distance L between the temperature sensors 4a and 5a are divided into ten sections and temperatures at boundaries of these sections are calculated at the commencement of each unit time interval $\Delta \theta$. The unit time interval $\Delta \theta$ may be set to any desired value within a range from 0.5 to 10.0 seconds. A temperature $t(x, \theta + \Delta \theta)$ at a point $P_i$ separated by a distance x from the first point $P_o$ after elapsing the unit time interval $\Delta \theta$ from a time $\theta$ can be calculated by the following difference equation. $t(x, \theta + \Delta \theta) = t(x, \theta) + C_1\{t(x - \Delta x, \theta) - 2t(x, \theta) + t(x + \Delta x, \theta)$56 wherein $$C_1 = \frac{\overline{\alpha} \cdot \Delta \theta}{\Delta x^2}$$

$\alpha$: average thermal diffusion coefficient

Upon effecting the above calculation, initial temperatures at points within the tire gauge and first boundary layer $B_1$ are set to the initial tire temperature and initial temperatures at points within the bladder and second boundary layer $B_2$ are set to the initial bladder temperature. As explained above, these initial temperatures are entered into the control unit 1 with the aid of the input unit 2.

In this manner, the temperature profile within the tire 30 can be estimated at the commencement of the predetermined unit interval $\Delta \theta$.

As is well-known, the bridging reaction of rubber during the vulcanization is a heat generating reaction and generated heat could not be ignored in order to increase the precision of the temperature estimation. Particularly, the influence of generated heat could not be ignored when the thickness of the rubber is thick. However, in the general FDM, the generated heat could not be introduced. According to the invention the average thermal diffusion coefficient $\alpha$ is changed in accordance with the progress of the vulcanization. That is to say, when the average thermal diffusion coefficient $\overline{\alpha}$ is increased with the increase of vulcanization V, it is possible to attain the temperature profile representing the actual temperature distribution much more precisely. In the present embodiment, the average thermal diffusion coefficient $\alpha$ is calculated by the following equation.

$$\overline{\alpha} = \overline{\alpha_0}\{1 + C(V)^n\}$$

wherein $\alpha_0$ . . . initial average thermal diffusion coefficient
C,n . . . constants determined by the composition of rubber
V . . . calculated least vulcanization By replacing $\alpha$ in the difference equation by $\alpha$ defined by the above equation, it is possible to calculate the temperature profile within the tire in a precise manner.

It should be noted that the influence of generated heat may be compensated for by various methods. For instance, a variation of the least vulcanization $\Delta V$ is first derived from the calculated vulcanization and then an amount of reaction heat $\Delta Q$ is calculated from $\Delta V$. Next, a temperature increase $\Delta t$ due to the reaction is derived from $\Delta Q$, and the calculated temperature profile is corrected by linear approximation using the derived $\Delta t$.

The estimation of the temperature profile within the tire may be effected by the finite element method (FEM) instead of FDM and similar results could be obtained. However, the FEM requires many more calculation steps than FDM, so that FDM is preferable.

Figure 8:
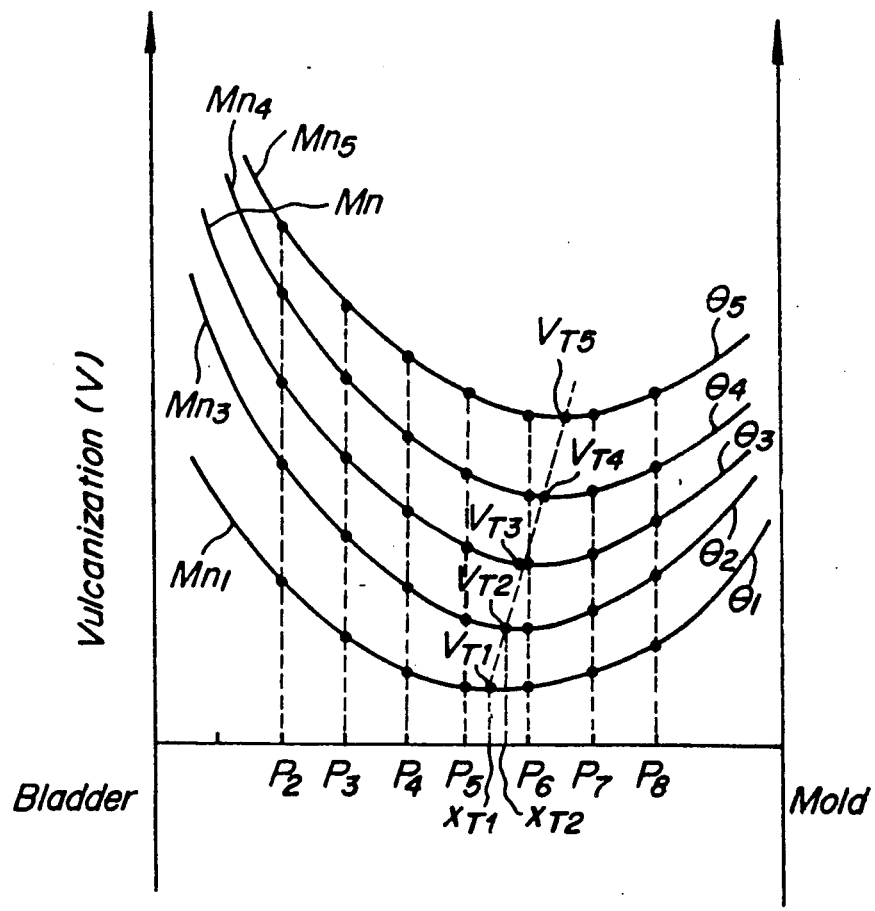
FIG. 8 is a graph representing the variation of vulcanization profile within the tire.

In a step $P_4$, the lowest temperature within the tire is compared with a given threshold temperature, e.g. 100° C. When the lowest temperature exceeds the threshold temperature, in a step $P_5$ a vulcanization profile is calculated from the temperature profile. As shown in FIG. 7, there are seven measuring points $P_2 \sim P_8$ within the tire vulcanization at these points are calculated from the estimated temperatures at these points. That is to say, an equivalent vulcanization V at respective point is calculated in accordance with the following Arrhenius equation at the commencement of each unit time interval $\Delta \theta$.

$$V = e^{-\frac{E}{R}(\frac{1}{T} - \frac{1}{T_0})} d\theta$$

wherein
E . . . activation energy
R . . . gas constant
$T_0$ . . . standard temperature
T . . . reaction temperature
$\theta$ . . . time In this manner, there are obtained vulcanization profiles as shown in FIG. 8 at the commencement of each time interval $\Delta \theta$. In FIG. 8, a horizontal axis denotes a position in the gauge direction of the tire and a vertical axis represents the extent of vulcanization. At a start time $\theta_1$ of the vulcanization calculating step $P_5$, there is derived a first vulcanization profile $M_{n1}$, and after the unit time interval $\Delta \theta$ has been elapsed, there is obtained a next vulcanization profile $M_{n2}$ at a time $\theta_2$. In this manner, at each times $\theta_1, \theta_2, \theta_3 \ldots$, there are derived vulcanization profiles $M_{n1}, M_{n2}, M_{n3} \ldots$ Next, in a step $P_6$, the least vulcanization is calculated by utilizing the method of least squares. Now, the process of deriving the least vulcanization will be explained. In general, a point of least vulcanization does not correspond to a temperature measuring point, so that the least vulcanization among the calculated values of vulcanization at the measuring points $P_2 \sim P_8$ could not be used as it is. Therefore, the least vulcanization is calculated from the vulcanization values at the measuring points. As shown in FIG. 8, a point of least vulcanization does not remain stationary, but is shifted toward the mold in accordance with the lapse of time.

The least vulcanization $V_{Ti}$ of respective vulcanization profiles may be calculated as follows by using the method of least squares. In the present embodiment, the vulcanization profile is expressed by a parabolic function.

$$V = Ax^2 + Bx + C$$

Deviations $d_i$ of the vulcanization values at respective points from the parabolic function are first derived and then a summation of squares of the deviations $$\sum_{i=2}^{8} d_i^2$$

is calculated. Next coefficients A, B and C are determined such that the above summation becomes minimum. Then the least vulcanization $V_{Ti}$ and a point $x_{Ti}$... at least vulcanization are calculated as follows.

$$\begin{cases} V_{Ti} = A(-B/2A)^2 + B(-B/2A) + C \\ x_{Ti} = -B/2A \end{cases}$$

It Should be noted that the least vulcanization can be derived by means of the method of least squares using other higher order functions than the parabolic function.

In the manner explained above, the least vulcanization is estimated from the vulcanization profile at the commencement of each unit time interval $\Delta\theta$. As explained above, in the present embodiment, the temperature measurement is carried out simultaneously at a plurality of portions of the tire, so that there are derived a plurality of vulcanization profiles at each time interval $\Delta\theta$ and a plurality of least vulcanization values are derived. Then the smallest value is selected from these plural least vulcanization values as the least vulcanization within the tire.

Step $P_7$ checks whether the estimated least vulcanization $V_T$ is within a given range or not at a predetermined timing $\theta_V$. That is to say, the least vulcanization $V_T$ is compared with maximum and minimum vulcanizations $V_{MAX}$ and $V_{MIN}$. At the same time, it is judged whether or not a given pressure has been applied to the bladder for a given time period $\theta_T$. When $V_{MAX} > V_T > V_{MIN}$ is satisfied and the pressure inside the bladder has had the given pressure over the given time period $\theta_T$, the real time mode is changed into the prediction mode in a step $P_8$. If $V_{MAX} > V_T > V_{MIN}$ is not satisfied, vulcanization is carried out under the real time mode for a predetermined time period as shown by a step $P_8$ in FIG. 5.

Figure 9:
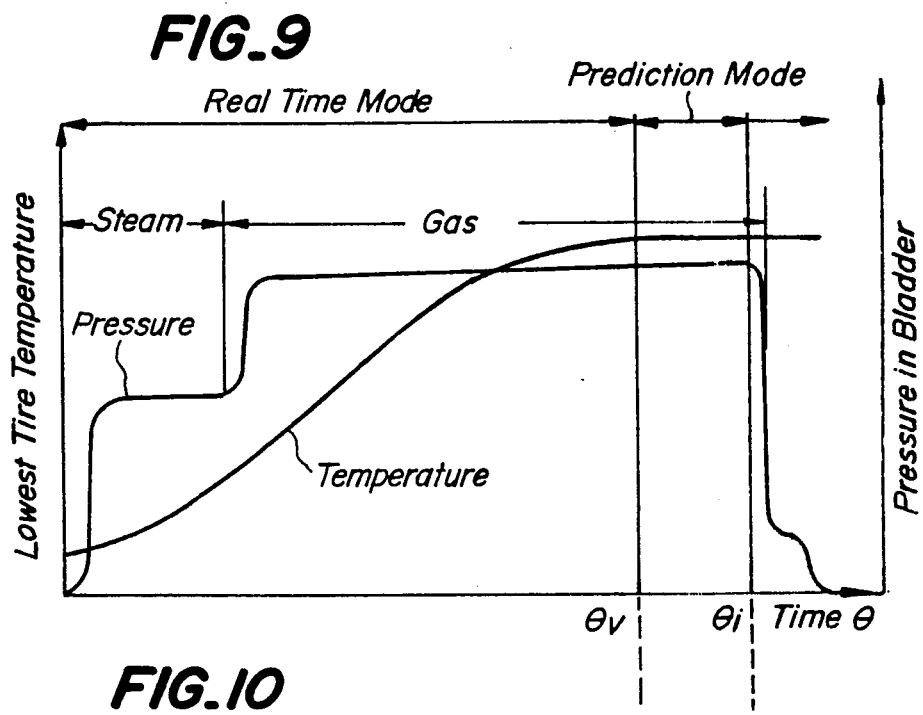
FIG. 9 is a graph showing the variation of lowest temperature.
Figure 10:
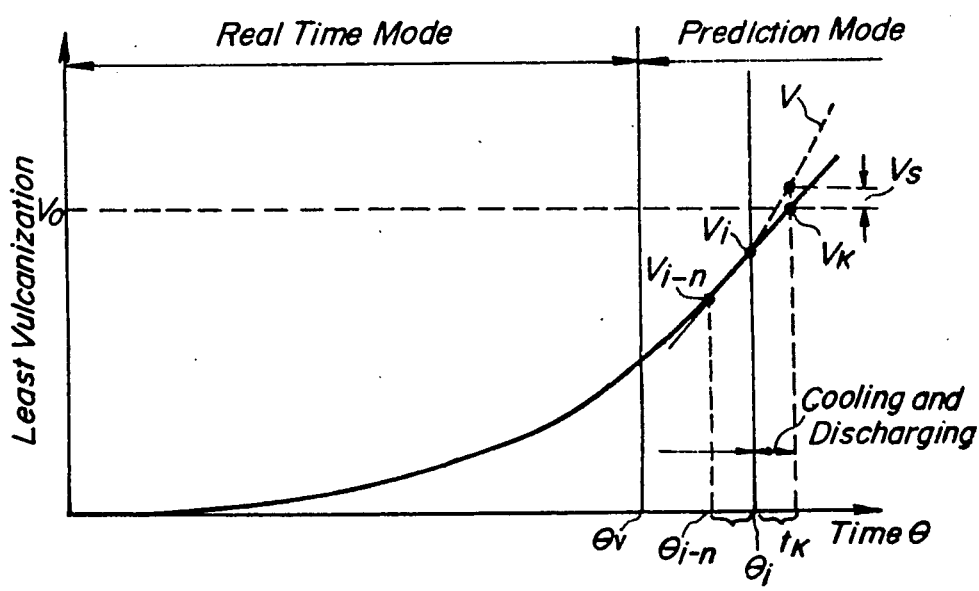
FIG. 10 is a graph representing the variation of least vulcanization.

According to the invention, it is possible to stop the vulcanizing process when the least vulcanization reaches a predetermined value. However, in the present embodiment, in order to control vulcanization much more precisely, the prediction mode for predicting the vulcanization after stopping the heat supply to the vulcanizing machine is introduced. That is to say, after the supply of the compressed and heated fluid medium into the and bladder is stopped at a timing $\theta_i$, the temperature within the tire is kept high as shown in FIG. 9 and the vulcanization further proceeds as depicted in FIG. 10. In FIG. 9, the temperature of the least vulcanization point is shown, and $\theta_V$ is the timing at which the real time mode is switched into the prediction mode in the normal cure. In the prediction mode, the least vulcanization is continuously predicted as shown by a step $P_{10}$.

In the prediction mode, a least vulcanization $V_K$ which will be attained after a time period $t_K$ will be elapsed from the stop of heat supply is predicted by a linear extrapolation using a least vulcanization $V_i$ at the timing $\theta_i$ and a least vulcanization $V_{i-n}$ at a timing $\theta_{i-n}$ i.e. a sample at n times before the instant $\theta_i$. The linear extrapolation is carried out on the basis of the following equation.

$$V_k = (V_i - V_{i-n})\frac{t_k}{t_n} + V_i$$

wherein $t_n = n \cdot \Delta\theta$

When the predicted least vulcanization reaches a desired vulcanization $V_o$, the heating is stopped at the timing $\theta_j$ as depicted in a step $P_{12}$. Then, in a step $P_{13}$, the vulcanizing process is finished and the prediction mode is changed into the real time mode. When the control unit 1 detects the vulcanization stop command, it supplies a vulcanization stop signal $C_4$ to the vulcanization stopping unit 36. Then, the vulcanization stopping unit 36 effects the cooling and discharging process in a usual manner. In FIG. 9, the variation in pressure inside the bladder 8a and the variation in temperature of the heating fluid mediums supplied to the bladder are also shown. When the abnormal condition is detected, the real time mode is exclusively applied and vulcanization is carried out for a predetermined time period.

Figure 11:
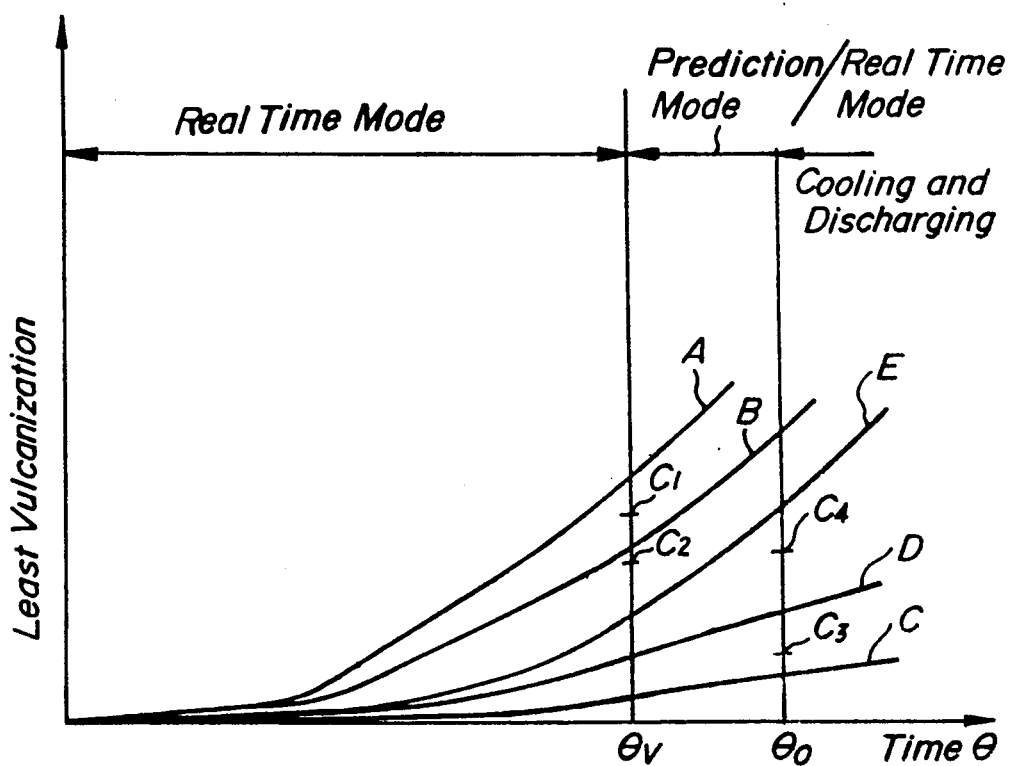
FIG. 11 is a graph showing the variation of least vulcanization under various abnormal conditions.

If the least vulcanization at the given time $\theta_V$ exceeds a predetermined upper threshold vulcanization $C_1$ as shown by a curve A in FIG. 11, the alarm is displayed and the vulcanization is stopped at a predetermined timing. In such a case, the real time mode is not changed into the prediction mode.

At the given time $\theta_V$, when the least vulcanization is between predetermined upper and lower threshold values $C_1$ and $C_2$ as illustrated by a curve B, the alarm is generated and the control is continued by the prediction mode.

At a predetermined vulcanization stop timing $\theta_o$, when the least vulcanization is smaller than a predetermined lower threshold value $C_3$ as shown by a curve C the alarm is displayed and the vulcanization is finished by the real time mode.

At the time $\theta_O$, when the least vulcanization exceeds the lower threshold value $C_2$, but does not exceed a lower threshold value $C_4$ as depicted by a curve D, the alarm is generated and the vulcanization is further carried out under the prediction mode. In FIG. 11, the variation of the usual or normal vulcanization is also expressed by a curve E.

By introducing the prediction mode as explained above, it is possible to control the vulcanization rate very precisely and over and under cure can be effectively prevented, so that the vulcanizing time period can be minimized. As shown in FIG. 10, when the prediction mode is not introduced, there might be produced an error in vulcanization amounting to $V_S$.

As explained above, in the vulcanization control method according to the invention, the temperature profile within the tire is estimated from the actually measured temperatures at the boundary between the mold and the tire and at the center post assembly of the bladder unit, then the vulcanization profile is calculated from the estimated temperature profile, and the least vulcanization is detected from the vulcanization profile. Therefore, even if the point of least vulcanization is shifted in the tire gauge direction, it is possible to detect the least vulcanization precisely, so that the vulcanization rate can be controlled in an accurate and reliable manner.

Further, in the present embodiment, after the least vulcanization has reached the predetermined value, the real time mode is changed into the prediction mode for predicting the least vulcanization which will be attained after the stop of the supply of heating fluids. By introducing the prediction mode, the increase in vulcanization during the cooling and discharging process can be taken into account so that the vulcanization rate can be controlled much more accurately, while any excessive vulcanization can be prevented effectively. Therefore, according to the invention the vulcanizing time can be minimized and an amount of the heating fluid mediums can be decreased materially, while desired characteristics of the vulcanized tire can be attained accurately and reliably.

Further, since the temperature sensor 5a for measuring the temperature within the bladder 8a is arranged at the center post assembly of the bladder unit, the temperature at the boundary between the tire and bladder can be estimated accurately. Moreover, the sensor is hardly damaged and the maintenance of the sensor can be improved.

The inventors have conducted various experiments and found that in case of a gas cure using the gas and steam heating fluids for the bladder unit, the temperature variation occurs in the circumferential direction of tire as well as in the axial direction of tire. Particularly, in the axial direction of tire there might be produced a relatively large temperature difference such as about 10° C. Therefore, the least cure point usually appears in the lower portion of the tire. Then, the heating time period is liable to be long and the efficiency of vulcanization could not be improved. In a preferred embodiment of the vulcanization control method according to the invention the above drawback can be mitigated in a simple manner.

Figure 12:
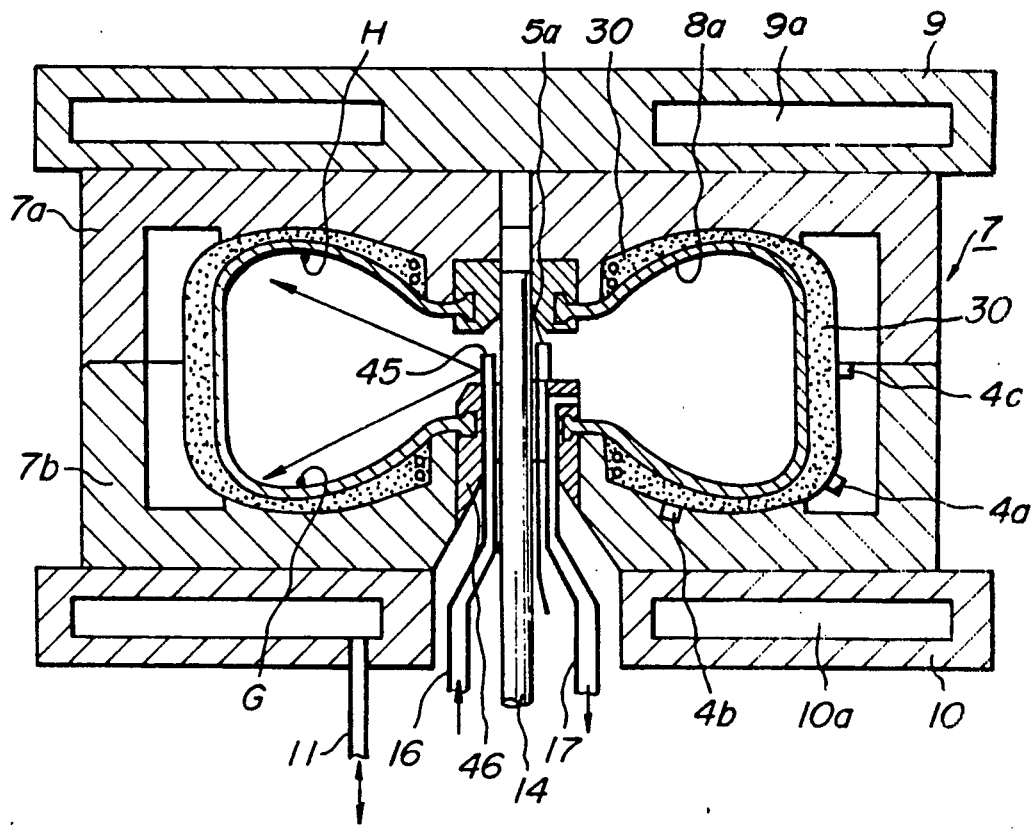
FIG. 12 is a schematic cross sectional view illustrating another embodiment of the vulcanization machine.
Figure 13:
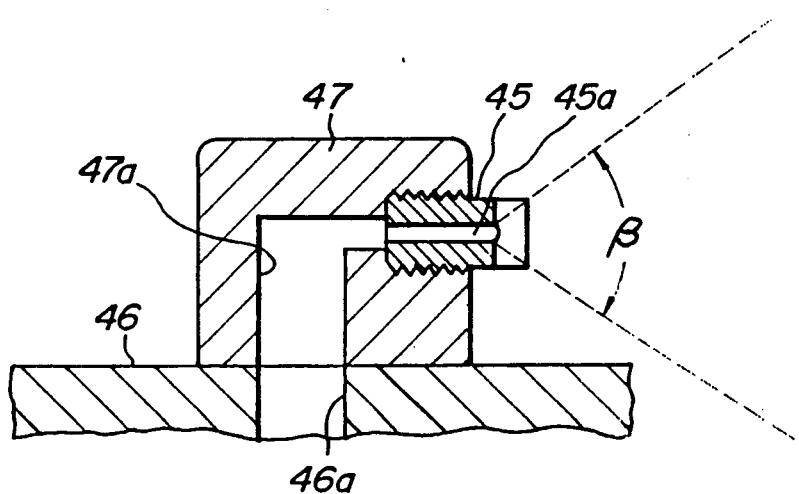
FIG. 13 is a cross sectional view depicting the detailed construction of the spray nozzle.

FIG. 12 is a schematic cross sectional view showing another embodiment of the vulcanizing machine. In the present embodiment, portions similar to those shown in FIG. 2 are denoted by the same reference numerals used in FIG. 2. In the present embodiment, in order to remove or decrease the temperature difference within the bladder 8a, the heated fluid is spread out of four spray nozzles 45 toward the inside of the bladder 8a. The nozzles 45 are spaced from each other by 90° viewed in the circumferential direction and are secured to a lower bladder ring assembly 46. As illustrated in FIG. 13, the spray nozzle 45 having a central conduit 45a is screwed into a mount 47 which is soldered to the lower bladder ring assembly 46 in such a manner that a conduit 47a formed in the mount 47 is communicated with a conduit 46a formed in the assembly 46. Then the heated fluid such as gas and steam is spread out of the nozzle 45 over a diffusion angle β of about 30°~45°, so that the injected fluid is sufficiently agitated in the bladder 8a and temperature within the bladder becomes uniform.

Figure 14:
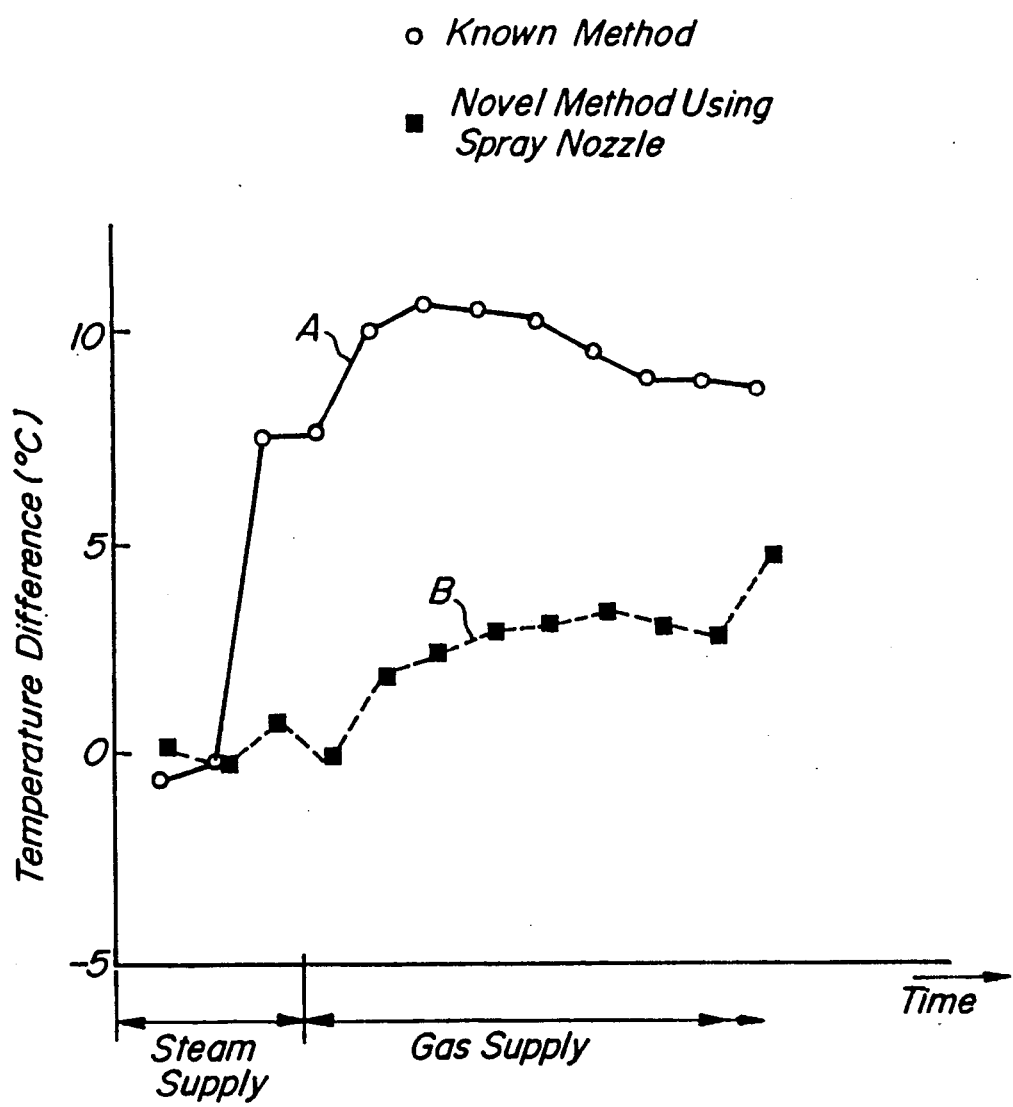
FIG. 14 is a graph showing the temperature difference within the bladder.

FIG. 14 shows graphs representing the temperature difference between points H and G on the upper and lower side portions of bladder 8a. A curve A denotes the known method in which the temperature difference amounting to more than 10° C. occurs. On the contrary, according to the invention, the temperature difference can be reduced lower than 5° C.

Figure 15:
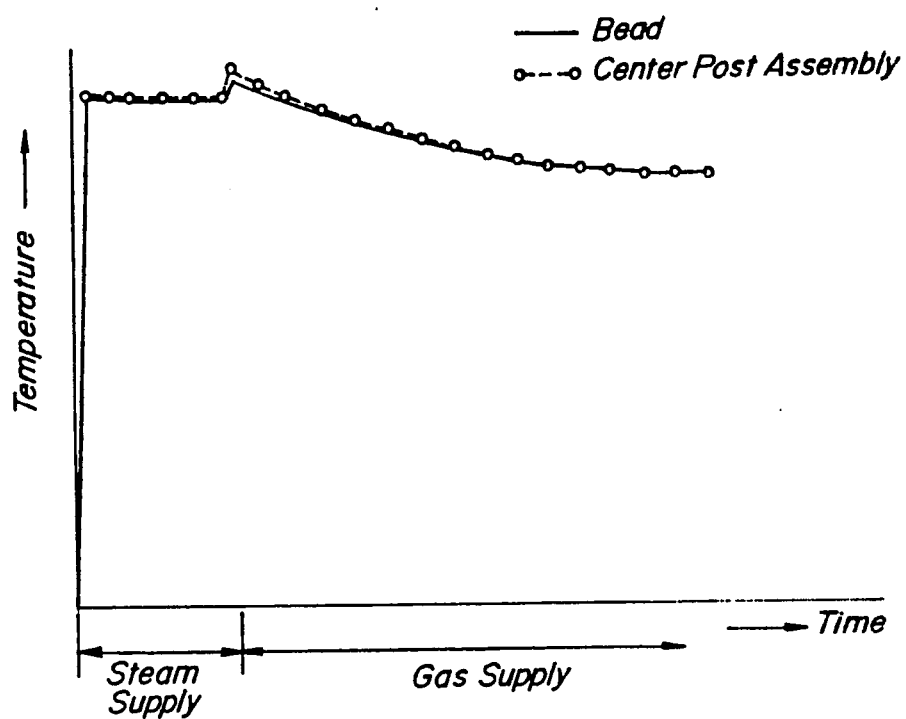
FIG. 15 is a graph representing the temperature variation within the bladder in the method according to the invention.
Figure 16:
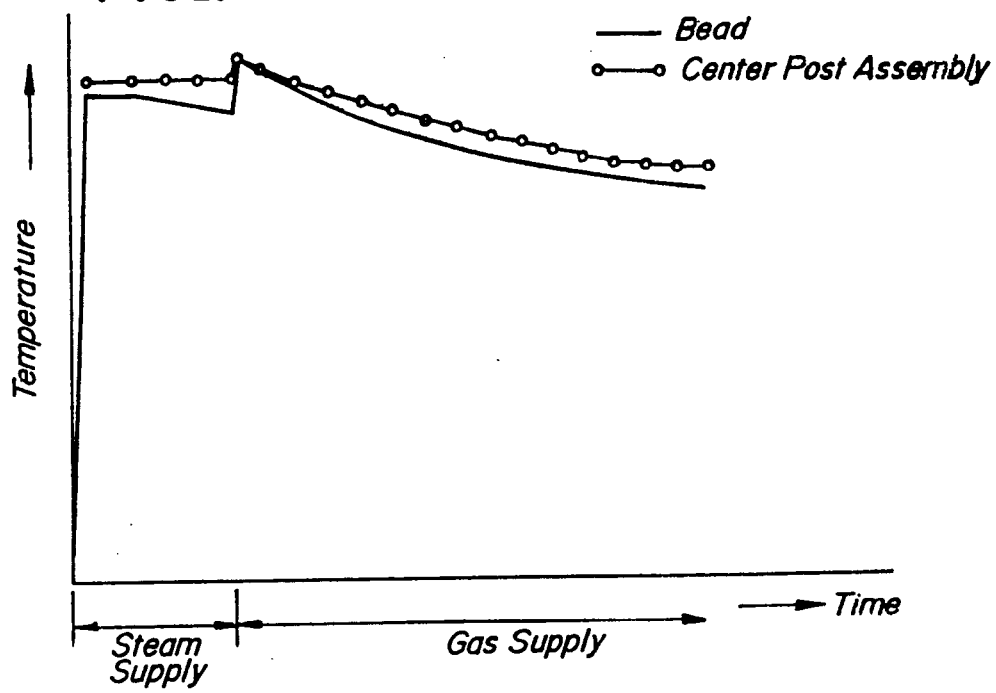
FIG. 16 is a graph depicting the temperature variation within the bladder in the known method.

FIG. 15 shows the temperature variation at the bead of tire and at the central post assembly of bladder unit in the method according to the invention. The temperature difference between these points is very small. FIG. 16 illustrates the temperature variation at these points in the usual method. The temperature difference between these points is rather large. It has been found that the temperature differences between the tread and shoulder of tire and the central post assembly of the bladder unit could be reduced to a large extent by using the spray nozzles 45 explained above.

Now several examples of the tire vulcanization controlling method according to the invention will be explained together with comparative examples, in which tires PSR 175 SR14 were vulcanized. The conditions other than the vulcanization were same for these examples. Characteristics of tire such as endurance of belt and carcass were measured by using an ordinary drum testing machine. After the tire was rotated for a predetermined time and predetermined load and speed, the endurance of belt and carcass was judged whether peal-off of edges of belt and carcass occurs or not and an extent of the peal-off, if existent. The test result will be shown in Table 1. In the Table 1, the various functions are denoted while values of the tire manufactured by the known method are normalized to 100.

TABLE 1

|  | Novel vulcanization method according to the invention | Known vulcanization control method |
|---|---|---|
| Productivity | 120 | 100 |
| Endurance |  |  |
| belt | 130 | 100 |
| carcass | 120 | 100 |

As can be read from the above table, according to the present invention the tire can be manufactured at a high reproductivity and the manufactured tire has superior characteristics.

Table 2 represents further examples of the tire vulcanization controlling method according to the invention together with comparative examples.

TABLE 2

|  | Example No. | | | | | |
|---|---|---|---|---|---|---|
|  | 1 | 2 | 3 | 4 | 5 | 6 |
| position of temperature measurement |  |  |  |  |  |  |
| mold side | A | D | C | A | A | A |
| bladder side | H | H | H | H | H | H |
| boundary layer |  |  |  |  |  |  |
| mold side | Yes | Yes | Yes | No | Yes | No |
| bladder side | Yes | Yes | Yes | Yes | No | No |
| treatment of complex construction | Yes | Yes | Yes | Yes | Yes | Yes |
| calculation method | FDM | FDM | FDM | FDM | FDM | FDM |
| temperature variation |  |  |  |  |  |  |
| tread surface | ±0.3° C. | ±0.4° C. | ±0.2° C. | ±10° C. | ±0.4° C. | ±10° C. |
| least cure point | ±0.5° C. | ±0.6° C. | ±0.4° C. | ±2.4° C. | ±2.7° C. | ±4.0° C. |
| ply | ±1.0° C. | ±1.0° C. | ±1.0° C. | ±1.0° C. | ±15° C. | ±15° C. |
| least vulcanization | ±0.1 | ±0.3 | ±0.1 | ±2.8 | ±3.0 | ±5.0 |
| vulcanizing time | ±0.5% | ±1.0% | ±0.4% | ±13% | ±15% | ±25% |
| reliability | ○ | ○ | ○ | XX | XX | XXX |
| maintenance | ○ | ○ | △ | ○ | ○ | ○ |

TABLE 2-continued

| | Example No. | | | | | |
|---|---|---|---|---|---|---|
| | 7 | 8 | 9 | 10 | 11 | 12 |
| step of calculation | ○ | ○ | ○ | ○ | ○ | ○ |
| position of temperature measurement | | | | | | |
| mold side | E | A | A | A | A | A |
| bladder side | H | K | I | M | H | H |
| boundary layer | | | | | | |
| mold side | Yes | Yes | Yes | Yes | Yes | Yes |
| bladder side | Yes | Yes | Yes | Yes | Yes | Yes |
| treatment of complex construction | Yes | Yes | Yes | Yes | No | No |
| calculation method | FDM | FDM | FDM | FDM | FEM | FDM |
| temperature variation | | | | | | |
| tread surface | ±4.0° C. | ±0.3° C. | ±0.3° C. | ±0.3° C. | ±0.3° C. | ±0.8° C. |
| least cure point | ±2.0° C. | ±0.4° C. | ±0.3° C. | ±4.0° C. | ±0.3° C. | ±1.5° C. |
| ply | ±1.3° C. | ±0.5° C. | ±0.3° C. | ±25° C. | ±0.3° C. | ±4.0° C. |
| least vulcanization | ±2.0 | ±0.1 | ±0.1 | ±5.0 | ±0.1 | ±1.5 |
| vulcanizing time | ±8.0% | ±0.3% | ±0.3% | ±25% | ±0.3% | ±6.0% |
| reliability | X | ○ | ○ | XX | ○ | X |
| maintenance | ○ | XXX | XXX | ○ | ○ | ○ |
| step of calculation | ○ | ○ | ○ | ○ | XXX | ○ |

Figure 17:
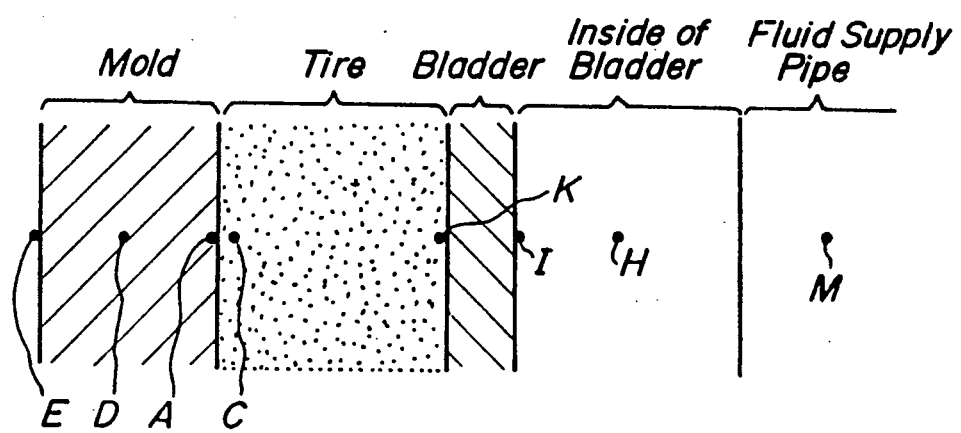
FIG. 17 is a schematic view illustrating various temperature measuring points.

In the above table 2, examples Nos. 1 to 3 are tires manufactured by the novel method according to the invention and examples Nos. 4 to 12 are tires vulcanized by the known method. The temperature measuring positions in the table 2 are shown in FIG. 17. It should be noted that the position A is the boundary between the mold and tire and the position C is in the tire surface. When the position C is adopted, there is formed a small hole in the tire surface, but in some tires such a small hole can be neglected. According to the invention the temperature on the bladder side is measured at the center position H of the bladder unit. The position M is in the inlet or outlet pipe connected to the bladder unit. The temperature variation at the tread surface and the least cure point should be smaller than ±1.0° C. and the temperature variation at the ply must be smaller than ±2.0° C. The variation of least vulcanization should be within ±0.5 when the ideal vulcanization is normalized to 10.0. The vulcanization time is defined as a deviation from the ideal vulcanization by percentages. The deviation of the vulcanization time should be smaller than ±2.0%. If the above values exceed respective threshold values, the precision and reliability of the control might be worse. As can be understood from the examples Nos. 4, 5 and 6, when the boundary layers are not introduced, the temperature profile within the tire can not be estimated accurately and there might be produced large deviations in the vulcanization. When the finite element method (FEM) is used as shown by the example No. 11, the temperature variation can be limited to small values, but the number of calculation steps becomes too large to be applied to the actual manufacturing.

It should be noted that the present invention is not limited to the embodiments so far explained, but various modifications and alternations could be conceived by those skilled in the art within the scope of the invention.

In the above embodiment, the temperatures at a plurality points at the shoulder, bead and tread are measured by temperature sensors 4a, 4b and 4c, but according to the invention it is also possible to measure a temperature at at least one point. For instance, it would be sufficient to measure a temperature at the shoulder or temperatures at the shoulder and bead.

Further, in the above embodiment, the second temperature sensor unit 5 comprises the single temperature sensor 5a arranged at the center post assembly, but two or more temperature sensors may be provided at the central post assembly.

Moreover, in the above embodiment, there are allotted nine points $P_1 \sim P_9$ between the temperature sensors, but the number of points may be determined at will be considering the precision to be attained and the calculation to be performed.

Further, in the above embodiment, the least vulcanization $V_k$ after stopping the heat supply to the vulcanizing machine is predicted by the linear extrapolation, but the least vulcanization can be estimated by any other method.

What is claimed is:

1. A method of controlling a tire vulcanization by controlling a heat supply to a vulcanizing machine which includes a mold unit and a bladder unit having a bladder and center post assembly comprising the steps of:

measuring a first temperature at at least one point at a boundary between the mold unit heated by steam and the tire during the tire vulcanization with a first temperature sensing means;

providing a second temperature sensing means at the center post assembly of the bladder unit heated by steam and gas during the tire vulcanization and measuring a second temperature with the second temperature sensing means;

introducing a first boundary layer between the first temperature sensing means and the tire;

introducing a second boundary layer between the second temperature sensing means and the bladder;

calculating temperatures at predetermined points within the tire from the first and second temperatures;

calculating vulcanizations at said predetermined points from said temperatures at said predetermined points;

estimating a vulcanization profile within the tire from said vulcanizations at said predetermined points;

detecting a least vulcanization of said vulcanization profile within the tire; and determining a timing at which the heat supply to the vulcanizing machine is stopped and producing a stop signal for the heat supply in accordance with said least vulcanization within the tire.

2. A method according to claim 1, wherein said first temperature sensing means comprises a plurality of temperature sensors arranged at or near a plurality of different portions of the tire, a plurality of least vulcanizations are derived from a plurality of vulcanization profiles each corresponding to respective portions of the tire, and said timing is determined in accordance with the least value among said plurality of least vulcanizations.

3. A method according to claim 2, wherein said plurality of portions of the tire are spaced from each other in a circumferential direction of the tire.

4. A method according to claim 2, wherein said plurality of portions of the tire are set at at least two of bead, shoulder and tread of the tire.

5. A method according to claim 1, wherein said step of calculating the temperatures comprises
calculating temperatures at a plurality of points by taking into account heat diffusion through said first and second boundary layers; and
deriving the temperature profile from temperatures at points within the tire.

6. A method according to claim 5, wherein said temperatures at a plurality of points are calculated by a finite difference method.

7. A method according to claim 5, wherein said temperatures at a plurality of points are calculated by a finite element method.

8. A method according to claim 6, wherein said temperatures calculating step comprises
entering thermal diffusion coefficients and thicknesses of said first and second boundary layers, the bladder and a plurality of components constructing the tire;
deriving an average thermal diffusion coefficient of said thermal diffusion coefficients; and
calculating said temperatures at said plurality of points in accordance with said first and second temperatures and average thermal diffusion coefficient.

9. A method according to claim 8, wherein said average thermal diffusion coefficient is corrected in accordance with an amount of heat generated by a vulcanization reaction within the tire.

10. A method according to claim 1; wherein said steps of calculating the temperatures estimating the vulcanization profile and deriving the least vulcanization are effected at a predetermined time interval.

11. A method according to claim 10, wherein said time interval is set to a value within a range from 0.5 second to 10.0 seconds.

12. A method according to claim 1, wherein said least vulcanization is derived by using a method of least squares.

13. A method according to claim 12, wherein said vulcanization profile is approximated by a parabolic function.

14. A method according to claim 1, further comprises
deriving the lowest temperature in the temperatures;
comparing the lowest temperature with a predetermined threshold temperature value; and
initiating the derivation of the vulcanization profile when the least temperature exceeds the threshold temperature value.

15. A method according to claim 1, further comprising
comparing the least vulcanization with predetermined upper and lower vulcanization threshold values;
changing a real time control mode into a prediction control mode when the least vulcanization is within said upper and lower vulcanization threshold values;
predicting a least vulcanization which will be attained during a cooling and discharging period after stopping the heat supply to the vulcanizing machine; and
determining said timing for stopping the heat supply to the vulcanizing machine when the predicted least vulcanization reaches a desired vulcanization.

16. A method according to claim 15, wherein said least vulcanization is predicted by using the least vulcanization derived from the vulcanization profile at a relevant time instant and at least one of the least vulcanization values derived from the vulcanization profiles at prior timings.

17. A method according to claim 16, wherein said least vulcanization is predicted by a linear extrapolation.

18. A method according to claim 1, wherein said first and second temperatures are measured under such a condition that a heated fluid is spread inside the bladder from a plurality of spray nozzles secured to the center post assembly of the bladder unit.

* * * * *